US00PP10758P

United States Patent [19]

Westhoff

[11] Patent Number: Plant 10,758

[45] Date of Patent: Jan. 19, 1999

[54] LOBELIA PLANT NAMED 'AZURO'

[76] Inventor: Heinrich Westhoff, Fresenhorst 22-24, 46354 Südlohn-Oeding, Germany

[21] Appl. No.: 888,344

[22] Filed: Jul. 3, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 221 1/1937 Johnson ..... Plt./68.1

*Primary Examiner*—Howard J. Locker
*Attorney, Agent, or Firm*—C. A. Whealy

[57] ABSTRACT

A distinctive cultivar of Lobelia, *Lobelia erinus L.,* plant named Azuro, Characterized by its compact and rounded plant habit; numerous dark blue flowers; early flowering; and long flowering period.

1 Drawing Sheet

The present invention relates to a new and distinct cultivar of Lobelia plant, botanically known as *Lobelia erinus L.,* and hereinafter referred to by the cultivar name Azuro. The new cultivar was discovered by the inventor in S üdlohn-Oeding, Germany, as a naturally-ocurring mutation of an unnamed cultivar of the species *Lobelia erinus L.* and was observed in a group of plants of the parent cultivar in the spring of 1991. Asexual reproduction of the new cultivar by cuttings in Südlohn-Oeding, Germany, has shown that the unique features of this new Lobelia are stable and are reproduced true to type in successive propagations. The new cultivar has not been observed under all possible environmental conditions. The phenotype may vary significantly with variations in environment such as temperature and light and fertility levels, without, however, any variance in genotype.

The following traits have been repeatedly observed and are determined to be the unique characteristics of Azuro:

1. Compact and rounded plant habit.
2. Numerous dark blue flowers.
3. Early flowering.
4. Long flowering period. The following characteristics differentiate the new Lobelia from the parent and from the species *Lobelia erinus L.:*

1. Plants of the new Lobelia are more compact and more rounded than plants of the parent cultivar and of the species *Lobelia erinus L.*
2. Plants of the new Lobelia have a more intense blue flower color than plants of the parent cultivar and of the species *Lobelia erinus L.*
3. Plants of the new Lobelia flower earlier and more profusely than plants of the parent cultivar and of the species *Lobelia erinus L.*
4. Plants of the new Lobelia flower for a longer period of time than plants of the parent cultivar and of the species *Lobelia erinus L.*

BRIEF DESCRIPTION OF PHOTOGRAPH

The accompanying colored photograph illustrates the overall appearance and flower color of the new Lobelia, showing the colors as true as it is reasonably possible to obtain in colored reproductions of this type. The photograph comprises a side perspective view of a typical hanging basket and a close-up view of typical flowers and leaves of Azuro. Actual flower and foliage colors may differ from flower and foliage colors in the photograph due to light reflectance.

DETAILED BOTANICAL DESCRIPTION

The following observations, measurements, values, and comparisons describe plants grown in Snohomish, Wash., under commercial greenhouse practice. In the following description, color references are made to The Royal Horticultural Society Colour Chart except where general terms of ordinary dictionary significance are used.

Botanical classification: *Lobelia erinus L.* cultivar Azuro.

Parentage: Naturally-occurring mutation of an unnamed cultivar of species *Lobelia erinus L.*

Propagation:

*Type.*—By cuttings.

*Time to initiate roots.*—About 12 days.

*Rooting habit.*—Root system is fibrous.

Plant description:

*Plant form.*—Upright and rounded perennial flowering plant. Freely branching with lateral branches forming at every node. Plants uniform in shape. Flowers abundant.

*Growth habit.*—Lateral shoots outwardly spreading, plants eventually becoming spherical in overall shape. Moderate to vigorous.

*Stem description.*—Lateral branch diameter: About 2 mm. Internode length: 3 to 5 cm. Stem color: 143A becoming brownish with development. Stem texture: Smooth.

*Foliage description.*—Leaf arrangement: Simple, alternate. Leaf length: About 5 cm. Leaf width: About 1.75 cm. Leaf shape: Linear to spatulate. Leaf apex: Acute. Leaf base: Attenuate, sessile. Leaf margin: Serrate, teeth on linear leaves are further apart than spatulate leaves. Leaf aspect: Mostly flat. Leaf texture: Smooth. Leaf color: Young foliage, upper and lower surfaces: 146A. Mature foliage, upper surface: 137A. Mature foliage, lower surface: 147B.

Flower description:

*Flowering habit.*—Star-shaped flowers arranged singly at lateral apices. Flowers held outwardly. Flowers persistent.

*Flower shape.*—Tubular with three larger lower petals and two upright petals.

*Natural flowering season.*—Spring through summer.

*Quantity of flowers.*—Numerous, plants flower continuously.

*Flowers.*—Diameter: About 2 cm. Height: About 1.5 cm.

*Peduncle.*—Strength: Flexible and wiry, but hold flowers outwardly. Color: 144A.

*Flower bud.*—Shape: Oblong. Diameter: About 2 mm. Length: About 1 cm. Color: Whitish green.

*Petals.*—Arrangement: In a circle, fused. Shape: Lower petals are elliptic and upper petals are narrowly oblong. Quantity per flower: Five. Length, above throat: Lower: About 7.5 mm. Upper: About 5 mm. Width: Lower: About 5 mm. Upper: About 1.5 mm. Apex: Cuspidate. Margin: Entire. Texture: Smooth and satiny. Color: When opening: Upper surface: 96C. Lower surfaces: 97B/97C. Fully open: Upper surface: 96B/96C with dark bluish purple spot, close to 89A, at base. Lower surface: 97A. Throat: White background with purple spots and two, white to bright yellow stripes.

*Sepals.*—Arrangement: Fused into a calyx, star-shaped. Shape: Narrowly lanceolate. Quantity per flower: Five. Calyx length: About 9 mm. Calyx diameter: About 2 mm. Apex: Acuminate. Margin: Entire. Texture: Smooth. Color: 146A.

*Reproductive organs.*—Stamens: Quantity: Five, fused. Filament color: White. Anther color: Whitish purple. Pollen amount: Moderate. Pistils: Length: About 9 mm. Stigma shape: Round. Stigma color: Purple. Style color: Green. Ovary color: Green.

Disease resistance: Resistance to known pathogens of Lobelia has not been observed.

Seed production: Seed production has not been observed.

I claim:

1. A new and distinct Lobelia, *Lobelia erinus L.,* plant named Azuro, as illustrated and described.

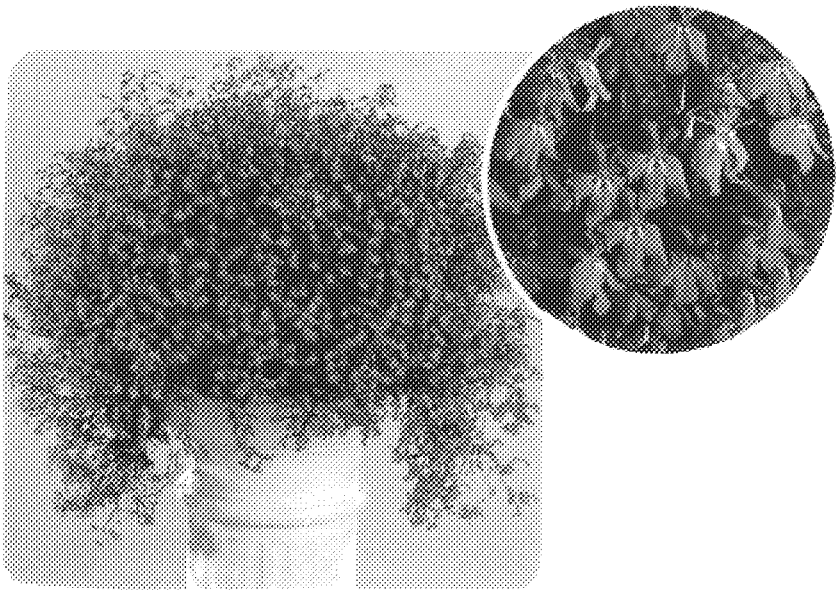

* * * * *